United States Patent [19]

Kilian et al.

[11] 4,010,545

[45] Mar. 8, 1977

[54] ADHESIVE BONDING TO TEETH OF ORTHODONTIC BRACKETS AND THE LIKE

[75] Inventors: Robert J. Kilian, East Amwell Township, Hunterdon County; John S. Gallagher, North Brunswick, both of N.J.

[73] Assignee: Johnson & Johnson, New Brunswick, N.J.

[22] Filed: Jan. 9, 1976

[21] Appl. No.: 647,845

[52] U.S. Cl. ............................................. 32/14 A
[51] Int. Cl.$^2$ ......................................... A61C 7/00
[58] Field of Search ............................. 32/14 A, 15

[56] References Cited

UNITED STATES PATENTS

| 3,250,003 | 5/1966 | Collito | 32/14 A |
| 3,962,267 | 8/1976 | Suzuki et al. | 32/15 |

*Primary Examiner*—Robert Peshock

[57] ABSTRACT

Orthodontic brackets and the like are adhesively secured to teeth by means of a self-curing thixotropic acrylic ester monomer composition wherein the monomer has been made thixotropic through the inclusion of fumed silane treated silica and wherein the acrylic ester monomer or monomers have two or more active acrylic ester groups, the thixotropic compositions prior to curing having a viscosity of about 85,000 cps to 4,385,000 cps.

Prior to adhering the orthodontic bracket or other device to the tooth surface, the tooth surface is acid-etched, rinsed and dried. The thixotropic-activated monomer is then applied to the surface of the tooth or to the surface of the orthodontic bracket just prior to placing the bracket on the tooth. The thixotropic acrylic ester monomer is activated prior to application by blending substantially equal proportions of a thixotropic monomer composition containing acrylic ester monomer, fumed silica, and amine activator with a thixotropic monomer composition containing acrylic ester monomer, fumed silica, and peroxide catalyst.

The bracket is adhered to the tooth surface through means of the thixotropic monomer mix and left undisturbed while being kept relatively dry until the monomer has hardened. Arch-wires may then be applied to the orthodontic bracket.

8 Claims, No Drawings

ADHESIVE BONDING TO TEETH OF ORTHODONTIC BRACKETS AND THE LIKE

BRIEF SUMMARY OF THE INVENTION

The advantage of being able to attach devices through adhesion directly to a tooth surface have long been recognized and substantial work has been done in trying to obtain a suitable procedure for obtaining such adhesive attachment. In an article appearing in the American Journal Orthodont, 58:21-40, Jul. 1970, titled: THE DIRECT BONDING OF ORTHODONTIC ATTACHMENTS TO TEETH BY MEANS OF AN EPOXY RESIN ADHESIVE, the authors discuss various problems associated with the generally used orthodontic attachments and various attempts which had, up to that time, been made in trying to solve these problems through the use of adhesives. The authors, Retief et al., refer to earlier work by Buonocore and others in which polyacrylic acid/zinc oxide dental cements were evaluated, and work by Bowen directed to adhesion between epoxy and tooth enamel surfaces. They also described their own efforts in which they used a particular epoxy composition as the adhesive. Although their particular epoxy composition was found to be superior to the other materials they had evaluated and appeared to be better than any of the other then available adhesive compositions, the same had definite disadvantages in that one had to wait fifteen to thirty minutes after placing the orthodontic brackets on the teeth before the patient was even permitted to rinse his mouth gently with warm water. Even then the archwires could not be placed until after three to seven days. Despite these precautions, a failure rate of twenty-two out of one hundred and two brackets applied was noted.

Other attempts to solve this problem of adhesively adhering orthodontic brackets to tooth surfaces resulted in the design of special clamp constructions whereby the orthodontic bracket, after applying the adhesive, was clamped onto the tooth surface and so held in place until the adhesive had cured sufficiently to permit the clamp's removal. Such a clamp arrangement is described, for example, in U.S. Pat. No. 3,787,976.

It has now been discovered that orthodontic brackets and similar devices can be adhesively bonded directly to a tooth surface and held in any desired position on the tooth without the necessity of clamps and the like, and the same become securely adhered to the tooth within a matter of a few minutes. This is of substantial advantage to the orthodontist and to the patient as it permits the attachment of the brackets and the arch-wires in the same sitting. The manner of attachment by which this is accomplished is to adhere the orthodontic bracket or other such device to a prepared tooth surface by using a catalyzed thixotropic acrylic or methacrylic ester monomer mix having a viscosity within the range of 85,000 cps to 4,385,000 cps. The acrylic or methacrylic ester monomers used have two or more active acrylic ester groups and the thixotropic monomer mix as applied contains, together with the polyacrylic ester monomer fumed silica for making the monomer thixotropic, an amine activator, and a peroxide catalyst.

Due to the thixotropic nature of the adhesive, the viscosity of the adhesive decreases while it is undergoing shear. Consequently, the adhesive can be prepared with a sufficiently high viscosity such that small amounts of the adhesive will not sag or flow under its own weight or when supporting a small light object such as an orthodontic bracket, but the adhesive will flow freely while undergoing shear such as that induced by hand mixing or by pressing an orthodontic bracket into the adhesive. When the shear is removed the adhesive returns to its highly viscous state. Thus, even though the adhesive has a sufficiently high viscosity to hold the bracket in place without sagging until the adhesive cures, the adhesive itself because of its thixotropic nature is easily mixed and applied and the tooth and bracket are readily wetted with the same.

The activated thixotropic monomer mix is prepared just prior to placing on the tooth surface or bracket by mixing together substantially equal parts of two thixotropic monomer compositions each having a viscosity within the range of 85,000 cps to 4,385,000 cps with one of the thixotropic monomer compositions containing a small amount of peroxide catalyst and the other thixotropic monomer composition containing a small amount of amine activator.

If the bracket or device to be adhered to the tooth is metal, the thixotropic monomer mix can be applied directly to the metal surface. However, if the orthodontic bracket is made of plastic, the surface of the plastic should first be treated with a mild solvent for the plastic prior to application of the thixotropic acrylic ester monomer mix. Where the plastic from which the orthodontic bracket is formed of a polycarbonate or similar resin the bracket surface to be adhered is first preferably wetted with methyl ethyl ketone or ethylene glycol dimethacrylate.

DETAILED DESCRIPTION OF INVENTION

As previously indicated, the desirability of being able to adhere an attachment such as an orthodontic bracket, directly to a tooth surface has been long recognized.

Various adhesive materials have been used and various methods of application tried. However, none of these have been fully satisfactory. Ideally, a bracket adhesive and its manner of application should be such as to give the orthodontist a maximum degree of flexibility with respect to the positioning and securing of the bracket while reducing the overall time for the adhesive to fully set so that the brackets may be firmly secured in place and the arch-wires placed all in one sitting. This not only reduces the discomfort to the patient but saves both the patient and the orthodontist substantial time.

It is necessary that the orthodontic bracket be correctly positioned on the tooth surface so as to properly direct the force of the arch-wires when applied. Should the bracket after being placed on the tooth surface tend to slide or shift in its position prior to the adhesive setting, the bracket then will not be in the precise position desired. As a result, the orthodontist is either required to hold the bracket in position until the adhesive has partially set so as to prevent the bracket from slipping or use special clamps to hold the same in place. This is both cumbersome and time consuming. Accordingly, it is highly desirable that a bracket adhesive should be of such nature that it has sufficient tack and initial internal strength that the adhesive itself will hold the bracket in the position in which it is placed without sliding or drifting but will still permit for a few minutes of repositioning by the orthodontist prior to setting if needed.

It is an object of the present invention to prepare an adhesive which will hold an orthodontic bracket on a tooth in the position in which it is placed by the orthodontist without the bracket sagging or sliding but will still permit adjustment on the tooth surface by the dentist for a brief time after initial positioning and will then set rapidly to hold the bracket in position.

It is a further object of the invention to prepare an adhesive that will directly bond orthodontic attachments to teeth in a way that is simple to use, that requires little time for use, that is aesthetically pleasing, and that provides sufficient adhesion to assure the retention of orthodontic attachments in the oral environment for over a year.

It is a further object of the present invention to prepare an adhesive that is self-curing within a few minutes after application to give a strong permanent bond to a tooth surface while at the same time it is nontoxic, nonirritating, and resistant to the oral environment which includes saliva food acid, and the strain and wear involved in the normal chewing of foods while eating. As eventually the orthodontic attachment must be removed it is a still further object of the present invention to apply the attachment in such manner and have an adhesive of such nature that the attachment can be easily removed from the tooth surface without tooth damage.

The above objects are accomplished by using, as the adhesive for directly bonding orthodontic attachments to teeth, catalyzed thixotropic polyacrylic ester monomers of the type generally used as binding agent in the preparation of highly filled tooth restorative composition such as described, for example, in U.S. Pat. Nos. 3,066,112; 3,539,533; and 3,835,090. These polyacrylic ester monomers, which include both the di- and triacrylate and methacrylate monomers such as described in the aforementioned patents, are made thixotropic through the inclusion of submicron silane treated silica. The silane treated fumed silica may be any of those generally available commercially where they are sold under trade names such as AEROSIL 972 by the Degussa Corporation and the silane treated CAB-O-SIL by the Cabot Corporation.

In the preferred practice of the present invention on acrylic ester monomer mix of bis-phenol A diglycidyl ether dimethacrylate, bis-phenol A dimethacrylate and triethylene glycol dimethacrylate is used together with AEROSIL 972.

As previously indicated, the thixotropic bracket adhesive composition of the present invention have a consistency such that the same will not flow, although readily wetting a surface to which they are applied. The adhesive prior to and immediately after activation has a viscosity of about 85,000 cps to 4,385,000 cps and when activated contains, together with the acrylic ester monomer and submicron silica, small amounts of amine activator and peroxide polymerization catalyst. The silane treated fumed silica is generally present in amounts of 6 to 11% by weight based on the total weight of the monomer and submicron silica present.

Initiation of the polymerization is conveniently affected at room temperature, e.g., about 25° to 30° C., by the inclusion in the adhesive formulation of the peroxide polymerization catalyst and the activator which functions to cause a rapid decomposition of the peroxide with the resultant formation of polymerization-inducing free radicals.

A variety of peroxide polymerization catalysts as known in the art can be used, benzoyl peroxide, 2-4-dichlorobenzoyl peroxide and 4-chlorobenzoyl peroxide being representative thereof. The catalyst is generally employed in amounts from 0.1 to 1.0% by weight based on the weight of active monomer or monomers present.

Similarly, an activator or accelerator material which cause decomposition of the catalyst is employed in the formulation, such as, for example, N,N-dialkylanilines and N,N-dialkyltoluidines.

The activator is generally employed in amounts ranging from about 0.1 to 1.0 weight percent based on the weight of the monomer or monomers present. While various activators can be used, amine activators of the type represented by the following formula are particularly effective:

wherein R is hydrogen or methyl and X is methyl, ethyl or hydroxyethyl. Preferred activators are N,N-di(2-hydroxyethyl)-p-toluidine, and N,N-di(2-hydroxyethyl)-3,4-dimethylaniline.

If desired, finely divided inorganic filler may also be included. However, inclusion of inorganic filler in amounts much in excess of about 60% by weight of the total composition is generally undesirable as it makes it more difficult to later remove the adhesive from the tooth surface. A variety of inorganic filler materials can be employed. Representative of such materials are silica, glass beads, aluminum oxide, fused silica, fused or crystalline quartz and the like. Where filler is included, the particle size of the filler material generally ranges from submicron to about 125 microns with the average particle size being in the range of about 15 to 30 microns and preferably is in the range of about 20 to 25 microns.

The particulate inorganic filler material where used should preferably be treated with a keying agent to improve the binding of the resin thereto. Keying agents and method of use are described in the aforementioned U.S. Pat. No. 3,066,112. Keying agents which have been found to be particularly suitable are the high performance ethylenically unsaturated organosilane compounds such as gammamethacryloxypropyltrimethoxysilane, vinyltrichlorosilane, vinyltriethoxysilane, vinyltrimethoxysilane, vinyltriacetoxysilane and the like.

The bracket adhesive as prepared for use by the orthodontist is in the form of a two component system hereinafter referred to for convenience as adhesive Component A and adhesive Component B. In the preferred practice of the present invention, adhesive Components A and B are substantially identical to each other differing primarily in that Component A contains the amine activator and Component B contains the peroxide catalyst. However, identical components need not necessarily be used and both the monomer mix and filler, where used, may differ somewhat in Component A from that used in Component B if desired, although identical monomer mixes are preferred.

When the adhesive is to be used, activation of the adhesive is initiated by mixing a small amount of adhesive of Component A with a small amount of adhesive of Component B with the activated adhesive then being applied to the prepared tooth surface. Although the viscosity of the adhesive is such as to hold the bracket in the position in which it is applied on the tooth, without slipping or sliding, the thixotropic nature of the adhesive permits easy mixing of Components A and B prior to application as well as easy application with good surface contact when applied to the relatively uneven tooth surface.

As previously indicated, the thixotropic nature and viscosity of the adhesive are important aspects of the adhesive of the present invention with respect to its use in placing of an orthodontic appliance on a tooth surface. Both Components A and B are thixotropic. Thus, the viscosity of the adhesive decreases while it is undergoing shear. Consequently, a small amount of adhesive will not sag or flow under its own weight, but while it is undergoing shear induced by hand mixing with a mixing stick or by pressing an orthodontic appliance into the adhesive, it flows very freely. Where the shear force is removed, the adhesive returns to its viscous state. Thus even though the adhesive has a high viscosity, which is needed to initially hold the appliance such as a bracket in place, it is easy to mix and manipulate. In practical terms the viscosity of the adhesive should be such that it shows no tendency to flow at normal room temperatures but with a mixing rate of about 1.5 or more revolutions per second with a mixing stick it will convert to a material that flows easily.

In order to further illustrate the invention the following example illustrating the present preferred form in which the invention is practiced is given. The example is given for the purposes of illustration only and it should be recognized that various other compositions can be made within the scope of the present invention following the teachings contained herein.

EXAMPLE I

| Component | TYPE OF COMPONENT | AMOUNT IN PART A | AMOUNT IN PART B |
| --- | --- | --- | --- |
| *Bis-GMA | Liquid | 63 | 63 |
| Bis-phenol A dimethacrylate | Soluble Solid | 7 | 7 |
| Triethylene glycol dimethacrylate | Liquid | 30 | 30 |
| N,N-di(2-hydroxyethyl)-p-toluidine | Soluble Solid | 2.448 | — |
| Benzoyl Peroxide | Soluble Solid | — | 2.040 |
| AEROSIL 972 | Insoluble Solid | 8.123 | 8.098 |

*BIS-GMA is the term generally used in the trade to identify the monomer: bis-phenol A diglycidyl ether dimethacrylate.

Both Components A and B are prepared in the following manner with the representative accelerator or peroxide being added to the monomer blend prior to the addition of the aerosil:

The bis-phenol A dimethacrylate is dissolved in the bis-GMA.

The remaining soluble solids are dissolved in the triethylene glycol dimethacrylate.

The bis-GMA solution is dissolved in the triethylene glycol dimethacrylate solution.

The aerosil is slowly added to the resulting solution. The resulting mixture is stirred until the aerosil is thoroughly wetted and uniformly distributed throughout the mixture.

Both Components A and B after preparation have the following physical properties:

In color, both A and B are off white and semi-transparent to translucent. The average viscosity of A as measured on a Brookfield Helipath Viscometer using spindle E is 259,000 cps, while the average viscosity of B measured in the same manner is 262,000 cps. The thixotropy of the two Components A and B is illustrated by the following Table which gives change in viscosity with shear rate. In practical terms, this implies that a mixing rate of 1.5 or more revolutions per second with a mixing stick will yield a material that flows easily.

| Shear Rate (Sec.$^{-1}$) | Viscosity (cps) |
| --- | --- |
| 0.907 | 322,575 |
| 1.814 | 215,050 |
| 3.628 | 136,850 |
| 7.256 | 85,531 |
| 14.512 | 54,984 |
| 41.000 | 25,951 |

The bond strength of this preferred adhesive as compared with bond strength of presently used and commercially available orthodontic adhesives is illustrated in the following Table where the other adhesives are identified solely by number. With the plastic brackets, bracket breakage occurred prior to bond failure. Accordingly, the values given for the plastic brackets are those recorded just prior to bracket breakage.

| FORMULATION | Time Period of Immersion of Samples in Water at 100° F (38° C) | Tensile Strength of brackets bonded to etched human enamel | |
| --- | --- | --- | --- |
| | | Metal PSI (SD) | Plastic PSI (SD) |
| Preferred Adhesive | 1 day | 1,276(158) | — |
| | 1 week | — | 777(26) |
| | 2 weeks | — | 740(51) |
| | 1 month | 910(196) | 756(26) |
| | 2 months | 1,082(148) | 699(110) |
| | 3 months | 1,022(77) | |
| Adhesive No. 1 | 1 day | 609(80) | 729(93) |
| | 1 week | — | 467(77) |
| | 2 weeks | — | 533(138) |
| | 1 month | — | 561(47) |
| | 2 months | — | 467(235) |
| Adhesive No. 2 | 1 day | 638(77) | 784(66) |
| Adhesive No. 3 | 1 day | 536(133) | 743(84) |
| Adhesive No. 4 | 1 day | 568(112) | 786(50) |

Using the above prepared adhesive, orthodontic brackets are placed on a patient's teeth in the following manner:

A prophylaxis is done on the enamel with a nonfluoride pumice paste.

The enamel is rinsed with water and dried with an air syringe.

The enamel is etched by swabbing it for 60 seconds with a cotton pellet which has been soaked in 35% phosphoric acid.

The enamel is rinsed clean with water and air dried for 30 seconds.

Equal amounts of the two pastes (Parts A and B) are mixed and then applied to the dry, etched enamel.

(Plastic brackets only) The bracket treatment is applied to the contact surface of the bracket with a brush or a cotton pellet and then the bracket is positioned onto the adhesive while the contact surface is moist with the treatment.

(Metal brackets only)—The bracket is positioned onto the adhesive.

The adhesive is allowed to harden. This takes approximately three minutes. During this period the bracket should not be touched or disturbed in any way.

A second mix of adhesive is prepared and used to cover the bracket flange.

Orthodontic brackets applied in the above manner after the adhesive has cured may be removed as follows:

The base of the bracket is grasped in the jaws of a pair of ligature cutters and then the bracket is snapped off the tooth by closing the jaws of the cutters. Any adhesive that remains on the tooth is scraped off with a dental scaler.

As previously indicated, the brackets may be relatively easily removed if the adhesive contains not more than 60 weight % of quartz filler or not more than 70% by weight of glass filler.

The adhesive of the present invention and the manner of using the same have many advantages for the orthodontist. The new adhesive system uses few components. It consists of two components, A and B, which are mixed in a one to one ratio to activate the adhesive. This one to one mix can be approximated by the eye and still insure a working time of within ten seconds of the stated ideal working time.

The only additional component is a pretreatment solution which is swabbed onto the contact surface of plastic attachments just prior to their bonding to metal. As previously indicated metal attachments do not require such a pretreatment. These few components lead to a short and simple application procedure which greatly reduces the chances of error in the use of material.

By using the two component systems, the one to one mix allows the orthodontist to prepare as much or as little adhesive as he needs with no perceived waste of material. Also the speed and use of the procedure greatly reduce the time which the orthodontist must spend with each patient. The thixotropic properties in combination with the high viscosity of the adhesive make it easy to pick up and transfer to the tooth surface the exact amount of material that is desired. Also, the adhesive immediately holds the orthodontic attachment in the desired position on the tooth regardless of the angle of inclination or the shape of the tooth surface with adhesive fully filling the space between the attachment and the tooth no matter how well or how poorly the surfaces may match in contour.

Furthermore, the adhesive will not flow or clog the wire channels of the attachments. The easy removal is also a substantial advantage as when the treatment is complete the orthodontic attachments may be easily removed and the remaining adhesive scaled from the tooth without the need of grinding. The semi-transparent to translucent nature of the adhesive allows the color of the tooth to show through thus allowing the coated areas to blend into the adjacent uncoated areas, while the rapid cure and high-bond strength permit placing of the orthodontic attachment together with the archwires all in one sitting resulting in a substantial saving of time both for the patient and for the orthodontist.

Having thus described our invention, we claim:

1. The method of adhering an attachment to a tooth surface comprising
    etching said tooth surface in the area to which said attachment is to be secured,
    placing said attachment on said etched tooth surface with a small amount of highly viscous thixotropic polyacrylic ester monomer composition between said attachment and said tooth surface, pressing said attachment against said tooth with said thixotropic monomer therebetween to wet the opposing surfaces of said tooth and attachment with said monomer and fill surface voids therebetween and curing said thixotropic monomer composition while said attachment is held on said tooth surface thereby.

2. The method of claim 1 in which said monomer composition has a viscosity of 85,000 to 4,385,000 cps.

3. The method of securing an attachment to a tooth surface comprising
    etching the tooth surface,
    mixing a thixotropic acrylic ester monomer composition containing an amine activator with a thixotropic acrylic ester monomer composition containing a peroxide catalyst to prepare an activated thixotropic acrylic ester monomer mix having a viscosity under nonagitated conditions within the range of 85,000 to 4,385,000 cps., placing said attachment on said etched tooth surface with said activated thixotropic mix between the opposed surfaces of said tooth and attachment, pressing said attachment against said tooth surface to assure wetting the tooth and attachment with said monomer composition, and leaving said attachment undisturbed on said tooth surface until the monomer has polymerized to firmly bond said attachment to said tooth surface.

4. The method of claim 3 wherein said tooth surface is etched by treating with a solution of phosphoric acid, water rinsed to remove said acid therefrom and then dried before applying said thixotropic mix.

5. The method of claim 3 wherein said thixotropic mix is prepared by mixing together in substantially equal proportion, a thixotropic composition having a viscosity under nonagitated condition of 85,000 to 4,385,000 cps., consisting essentially of polyacrylic ester monomer, silane treated fumed silica, and a small amount of an amine activator and a thixotropic composition having a viscosity under nonagitated condition of 85,000 to 4,385,000 cps consisting essentially of polyacrylic acid monomer, silane treated fumed silica, and peroxide catalyst, said fumed silica being present in each of said compositions in an amount of 6 to 11% by weight.

6. The method of claim 5 in which said submicron silica is a silane treated fumed silica.

7. The method of claim 6 in which the monomer content of both of the thixotropic acrylic ester monomer compositions is made up of the monomers bis-phenol A diglycidyl ether dimethacrylate, bis-phenol A dimethacrylate, and triethylene glycol dimethacrylate.

8. The method of claim 5 in which said amine activator is N,N-di(2-hydroxyethyl)-p-toluidine and said peroxide catalyst is benzoyl peroxide.

* * * * *